United States Patent
Roth (10) Patent No.: US 11,035,841 B2
(45) Date of Patent: Jun. 15, 2021

(54) MONITORING THE PERFORMANCE OF PROTECTIVE FLUIDS IN DOWNHOLE TOOLS

(71) Applicant: Saudi Arabian Oil Company, Dhahran (SA)

(72) Inventor: Brian A. Roth, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/506,612

(22) Filed: Jul. 9, 2019

(65) Prior Publication Data

US 2021/0010995 A1    Jan. 14, 2021

(51) Int. Cl.
| | |
|---|---|
| *G01N 33/28* | (2006.01) |
| *E21B 47/008* | (2012.01) |
| *E21B 43/12* | (2006.01) |
| *G01N 27/22* | (2006.01) |

(52) U.S. Cl.
CPC ....... *G01N 33/2888* (2013.01); *E21B 43/128* (2013.01); *E21B 47/008* (2020.05); *G01N 27/22* (2013.01)

(58) Field of Classification Search
CPC . E21B 43/128; E21B 47/008; G01N 33/2888; G01N 27/22
See application file for complete search history.

(56) References Cited

U.S. PATENT DOCUMENTS

| | | | | |
|---|---|---|---|---|
| 4,728,882 | A | * | 3/1988 | Stanbro .............. G01N 27/227 204/400 |
| 5,597,042 | A | | 1/1997 | Tubel et al. |
| 5,754,055 | A | * | 5/1998 | McAdoo .............. G01N 22/02 324/553 |

(Continued)

FOREIGN PATENT DOCUMENTS

| | | |
|---|---|---|
| GB | 2302114 | 1/1997 |
| GB | 2302349 | 1/1997 |

(Continued)

OTHER PUBLICATIONS

PCT International Search Report and Written Opinion in International Appln. No. PCT/US2020/041329, dated Oct. 22, 2020, 15 pages.

(Continued)

*Primary Examiner* — John Fitzgerald
(74) *Attorney, Agent, or Firm* — Fish & Richardson P.C.

(57) ABSTRACT

A method of monitoring a protective fluid of a wellbore tool includes flowing, by a sensor or a fluid moving device secured to a wellbore tool disposed at a downhole location within a wellbore, a portion of a protective fluid of the wellbore tool through a body of the sensor. The portion of the protective fluid is exposed to the body of the sensor responsive to the flowing. The protective fluid degrades over time responsive to the wellbore tool performing operations in the wellbore. The method also includes, in response to the protective fluid being exposed to the body of the sensor, determining, at least in part by the sensor, a degradation (Continued)

level of the protective fluid. The method also includes transmitting, by the sensor or a device communicatively coupled to the sensor, the determined degradation level to a surface of the wellbore.

20 Claims, 6 Drawing Sheets

(56) References Cited

U.S. PATENT DOCUMENTS

| | | | | |
|---|---|---|---|---|
| 5,973,503 | A * | 10/1999 | Kuipers | G01N 33/2847 324/439 |
| 6,199,629 | B1 | 3/2001 | Shirk et al. | |
| 6,392,562 | B1 * | 5/2002 | Boston | G01N 15/0656 324/204 |
| 6,459,995 | B1 * | 10/2002 | Collister | G01N 27/221 702/23 |
| 6,535,001 | B1 | 3/2003 | Wang | |
| 6,590,402 | B2 * | 7/2003 | Wang | G01N 27/06 324/663 |
| 6,718,819 | B2 * | 4/2004 | Schoess | B01D 27/08 210/167.02 |
| 7,129,715 | B2 * | 10/2006 | Hayashi | G01N 33/2888 324/685 |
| 8,508,741 | B2 | 8/2013 | Kumar | |
| 8,522,604 | B2 * | 9/2013 | Zhe | G01M 13/02 73/61.71 |
| 9,804,076 | B2 * | 10/2017 | Harrell | G01N 33/2823 |
| 2004/0084189 | A1 | 5/2004 | Hosie et al. | |
| 2004/0250606 | A1 * | 12/2004 | Buttgenbach | G01N 33/2888 73/61.49 |
| 2006/0076149 | A1 | 4/2006 | McCalvin | |
| 2006/0105467 | A1 * | 5/2006 | Niksa | G01N 27/126 436/150 |
| 2009/0120168 | A1 | 5/2009 | Harrison et al. | |
| 2009/0153155 | A1 * | 6/2009 | Chambon | G01N 33/03 324/698 |
| 2010/0109686 | A1 * | 5/2010 | Zhe | G01M 13/02 324/698 |
| 2014/0024073 | A1 | 1/2014 | Zhdaneev et al. | |
| 2014/0116117 | A1 * | 5/2014 | Joksch | G01N 27/22 73/61.44 |
| 2014/0158347 | A1 | 6/2014 | Fielder et al. | |
| 2015/0209782 | A1 * | 7/2015 | Mostowfi | G01N 33/2823 422/503 |
| 2016/0195509 | A1 * | 7/2016 | Jamieson | G01N 33/2888 356/70 |
| 2016/0363575 | A1 * | 12/2016 | Von Herzen | G01N 33/2888 |
| 2018/0051700 | A1 | 2/2018 | Sheth et al. | |
| 2018/0347346 | A1 | 12/2018 | Gouda et al. | |
| 2019/0204291 | A1 * | 7/2019 | Potyrailo | G01N 27/026 |
| 2020/0096431 | A1 * | 3/2020 | Nie | F16N 29/04 |

FOREIGN PATENT DOCUMENTS

| | | |
|---|---|---|
| NO | 20140453 | 10/2015 |
| WO | WO 2009090466 | 7/2009 |
| WO | WO 2009137316 | 11/2009 |
| WO | WO 2014151967 | 9/2014 |
| WO | WO 2020002946 A1 * | 2/2020 |

OTHER PUBLICATIONS

Aghayan, "On-Line Monitoring of Engine Health through the Analysis of Containments in Engine. Lubricant," University of Western Ontario (Graduate Program in Mechanical and Material Engineering), May 2012, 274 pages.

Kauffman, "Rapid, Portable Voltammetric Techniques for Performing Antioxidant, Total Acid No. (TAN) and Total Base No. (TBN) Measurements," Technology Showcase: Integrated Monitoring, Diagnostics and Failure Prevention, Proceedings of a Joint Conference, Apr. 22-26, 1996, 13 pages.

Meredith et al., "Influence of biodegradation on crude oil acidity and carboxylic acid composition," Organic Geochemistry vol. 31, 2000, 15 pages.

Wang, "Engine oil condition sensor: method for establishing correlation with total acid number," Sensors and Actuators B, vol. 86, 2002, 5 pages.

Wilson, "Determination of the asphaltene and carboxylic acide content of a heavy oil using a microfluidic device," Lab on a Chip, Apr. 2009, 6 pages.

Zhang, "A novel on-chip impedance sensor for the detection of particle contamination in hydraulic. oil," micromachines, MDPI, Aug. 14, 2017, 15 pages.

* cited by examiner

MONITORING THE PERFORMANCE OF PROTECTIVE FLUIDS IN DOWNHOLE TOOLS

FIELD OF THE DISCLOSURE

This disclosure relates to monitoring protective fluids of wellbore equipment. More specifically, this disclosure relates to monitoring protective fluids of electric submersible pumps ("ESP") and other wellbore tools.

BACKGROUND OF THE DISCLOSURE

Wellbore tools have protective fluids such as lubricants and dielectric fluids to protect rotary components and electric components inside the wellbore tools. The protective fluids can degrade over time due to heat, pressure, water ingress, or contamination from the production environment. Methods and systems for monitoring the degradation of protective fluids are sought.

SUMMARY

In one embodiment, a method of monitoring a protective fluid of a wellbore tool is disclosed. The method includes flowing, by a sensor or a fluid moving device secured to a wellbore tool disposed at a downhole location within a wellbore, a portion of a protective fluid of the wellbore tool through a body of the sensor. The portion of the protective fluid is exposed to the body of the sensor responsive to the flowing. The protective fluid degrades over time responsive to the wellbore tool performing operations in the wellbore. The method also includes, in response to the protective fluid being exposed to the body of the sensor, determining, at least in part by the sensor, a degradation level of the protective fluid. The method also includes transmitting, by the sensor or a device communicatively coupled to the sensor, the determined degradation level to a surface of the wellbore.

In some implementations, the sensor includes a microfluidic device, and determining the degradation level includes analyzing, by the microfluidic device, the protective fluid to determine the degradation level of the protective fluid.

In some implementations, the protective fluid is flowed through a sensory convection current of fluid flowing through the wellbore.

In some implementations, flowing the protective fluid includes moving the fluid by at least one of a peristaltic pump or an Archimedes screw-type pump.

In some implementations, the wellbore tool includes an electric submersible pump (ESP) coupled to a monitoring sub on which the sensor is secured, the monitoring sub communicatively connected to the surface of the wellbore, and transmitting the degradation level to the surface includes sending, from the sensor, the degradation level to the monitoring sub, and sending, from the monitoring sub, the degradation level to the surface.

In some implementations, the sensor includes a microfluidic device, and determining the degradation level includes determining the degradation level using at least one of an inductance detection technique and a capacitance change technique.

In some implementations, the microfluidic device is disposed along a flow path of the protective fluid, and determining the degradation level of the protective fluid includes using a fluid moving device to flow a portion of the protective fluid through a micro-channel of the microfluidic device.

In some implementations, determining the degradation level includes detecting a change in inductance and an increase in a signal to noise ratio of the microfluidic analyzer as a portion of the protective fluid moves through the channel using the inductance detection technique.

In some implementations, the protective fluid includes at least one of a dielectric fluid or a hydraulic fluid.

In some implementations, transmitting the determined degradation level includes transmitting at least one of a voltage output, a current output, a pressure output, a time stamp, and a temperature output of the sensor.

In some implementations, the method further includes determining, at least in part by a surface processor at the surface of the wellbore, the degradation level of the protective fluid.

In another embodiment, a system for monitoring a protective fluid of an electric submersible pump is disclosed. The system includes a monitoring sub coupled to an electric submersible pump. The monitoring sub is communicatively coupled to a surface of a wellbore. The system also includes a microfluidic device communicatively connected to the monitoring sub, the microfluidic device configured to be exposed to a protective fluid of the ESP as a portion of the protective fluid is flowed through a body of the microfluidic device responsive to the protective fluid. The microfluidic device is configured to, at least in part, determine a degradation level of the protective fluid and transmit the degradation level to the monitoring sub to be transmitted, by the monitoring sub, to the surface of the wellbore.

In some implementations, the system further includes a fluid moving device configured to move the protective fluid across a surface of the body of the microfluidic device.

In some implementations, the fluid moving device includes at least one of a peristaltic pump or an Archimedes screw-type pump.

In some implementations, the protective fluid includes at least one of a dielectric fluid and a hydraulic fluid.

In some implementations, the protective fluid degrades over time responsive to the ESP performing operations in the wellbore.

In some implementations, the microfluidic device is configured to determine the degradation level using at least one of an inductance detection technique and a capacitance change technique.

In some implementations, the microfluidic device is disposed along a flow path of the protective fluid, where a fluid moving device is configured to flow a portion of the protective fluid through a micro-channel of the microfluidic device.

In some implementations, the microfluidic device is configured to use the inductance detection technique, and the microfluidic device is configured to determine the degradation level by detecting a change in inductance and an increase in a signal to noise ratio in the microfluidic device as a portion of the protective fluid moves through the channel.

In some implementations, the device is configured to transmit the determined degradation level by transmitting at least one of a voltage output, a current output, a pressure output, a time stamp, and a temperature output of the microfluidic device.

DETAILED DESCRIPTION OF THE DISCLOSURE

This disclosure relates to methods and systems of monitoring a protective fluid of wellbore equipment to prevent the failure of the wellbore equipment. More specifically, this disclosure relates to the use of microfluidic devices such as microfluidic analyzers to monitor and analyze the protective fluid of electric submersible pumps (ESPs) and other wellbore equipment.

Particular implementations of the subject matter described in this specification can be implemented so as to realize one or more of the following advantages. For example, monitoring the protective fluids of wellbore tools can prevent the failure of the wellbore tools. The inclusion of a microfluidic analyzer in an ESP can provide early detection of the fluid degradation, which can minimize disruption to production since a rig could be scheduled before the equipment fails in place.

Figure 1:
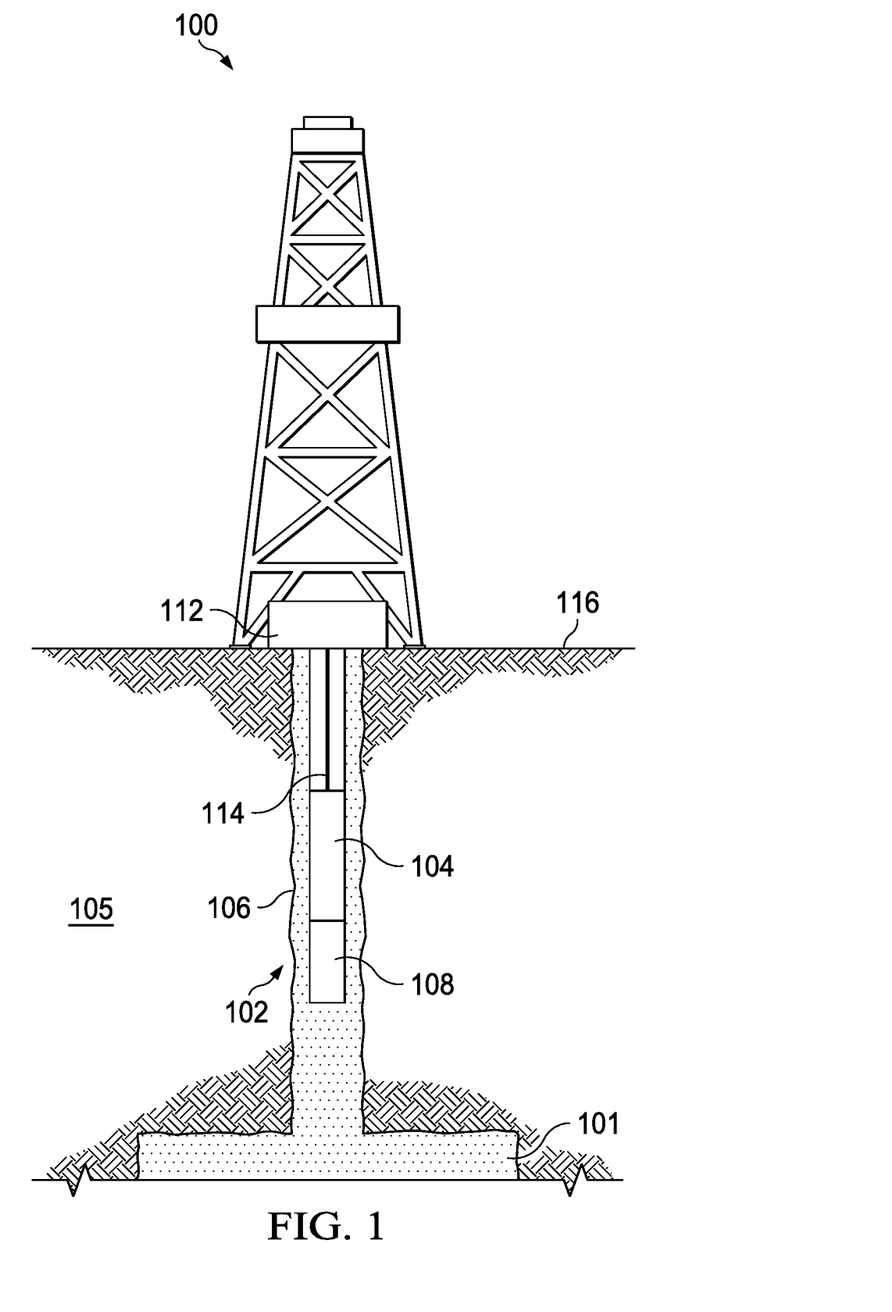
FIG. 1 is a cross-sectional, schematic view of a monitoring system deployed in a wellbore.

Referring to FIG. 1, a method and system 100 for monitoring a protective fluid of a pump (for example, an ESP) 104 is shown. The monitoring system 100 includes an ESP assembly 102 disposed at a downhole location within a wellbore 106 formed in a geologic formation 105. The geologic formation 105 includes a hydrocarbon reservoir 101 from which hydrocarbons can be extracted. The ESP assembly 102 features a pump 104 and a monitoring sub 108. The system 100 also includes a communication line 114 and a receiver 112. The communication line 114 connects the monitoring sub 108 to the receiver 112. The receiver 112 can be on the wellhead or at a different location at the surface 116 of the wellbore 106. The receiver 112 can include a processor configured to process the information received from the monitoring sub 108.

Wellbore tools such as logging tools can be considered temporary, with lifetime in the wellbore 106 measured in hours or days. Permanent equipment or tools may include downhole gauges, inflow control valves, subsurface safety valves, and wellhead equipment including subsea trees. Semi-permanent wellbore tools include equipment such as ESPs, which have a limited lifetime in the well, with expected duration measured in months or years. Some of these wellbore tools may contain protective fluid in cavities of the tool to provide lubrication for bearings, heat dissipation for electrical equipment, or dielectric protection for electrical and electronic equipment. With time, heat and possible contamination from the production environment can cause the protective fluid in the equipment to degrade. Without knowing the degradation level of the protective fluid, the fluid can degrade past its useful life and can lead to failure of the respective wellbore tool.

In the production environment (for example, inside the wellbore, the wellhead, or the reservoir) of oil and gas, some equipment or wellbore tools may be deployed either temporarily, permanently, or semi-permanently. The technology described herein can be implemented in any wellbore tool regardless of its respective lifetime. As further shown in FIG. 3, a sensor exposed to the protective fluid can determine the degradation level or the quality of the fluid. For example, 'a lab-on-a-chip' that includes a microfluidic device (for example, a microfluidic analyzer) coupled to a surface of a wellbore tool can be used to analyze the protective fluid of the tool and determine a degradation level of the protective fluid. By analyzing the protective fluid, decisions regarding replacing the protective fluid of the downhole tools or similar maintenance-related decisions to prevent the failure of the wellbore tool can be made. The degradation level determined by the sensor can be transmitted, in some implementations, to the monitoring sub 108. As shown in FIG. 1, the monitoring sub 108 is communicatively connected to the wellhead surface 116 via communication line 114 (or wirelessly). The monitoring sub 108 can transmit the degradation level determined by the microfluidic device to the surface 116. For example, the monitoring sub 108 can transmit, along with other ESP data, the degradation level to receiver 112. In some implementations, the data received can be analyzed (or further analyzed) in real time at the surface, and alarms or triggers can be activated if the degradation level is above a specific threshold. By "real time," it is meant that a duration between receiving an input and processing the input to provide an output can be minimal, for example, in the order of milliseconds, microseconds or nanoseconds.

Figure 2:
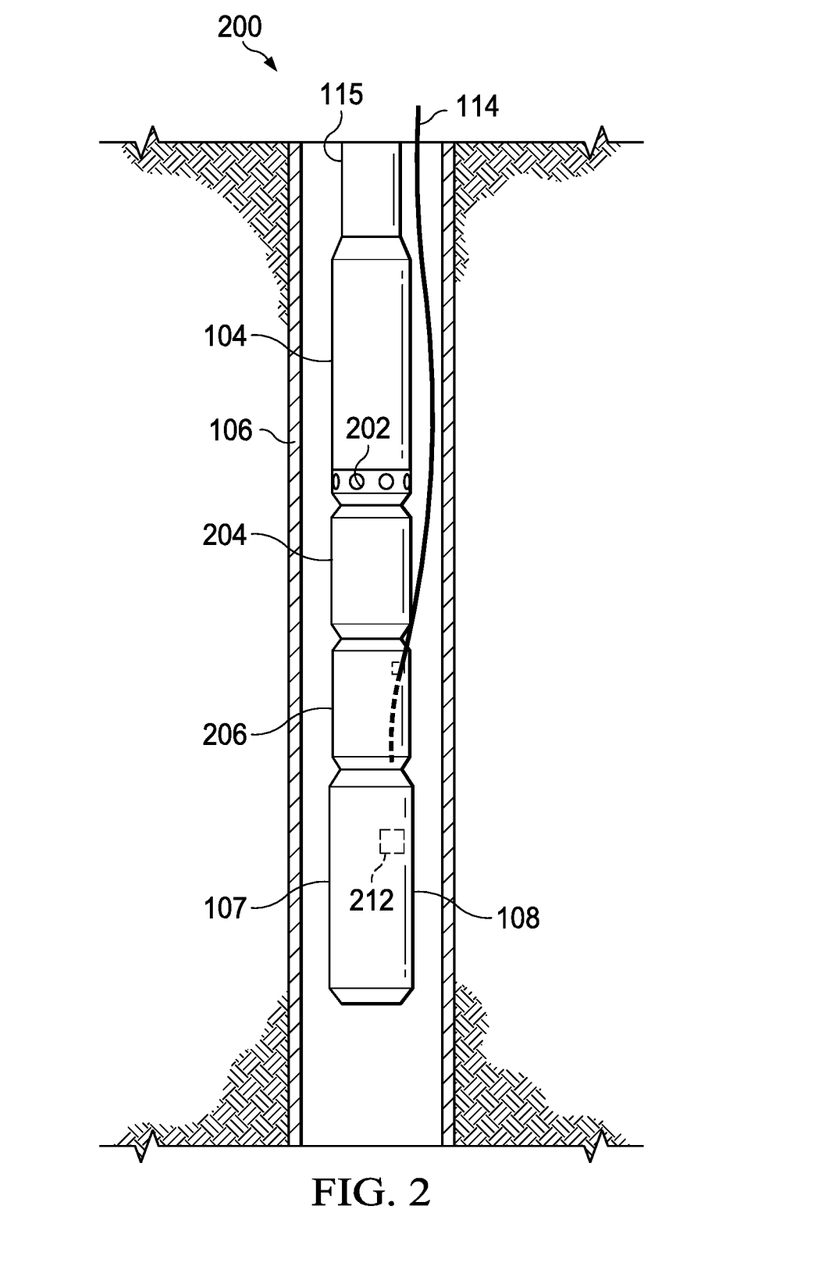
FIG. 2 shows an ESP assembly according to an implementation of the present disclosure.

FIG. 2 illustrates an ESP assembly 200 deployed at the wellbore 106. The ESP assembly 200 includes a pump 104, a pump intake 202, a protector 204, a motor 206, and a monitoring sub 108 communicatively connected, via communication line 114 (which may include a power line connected to motor 206), to the surface. The communication line 114 can be coupled to a tubing assembly 115 that connects the ESP assembly to the surface. The monitoring sub 108 is coupled to the motor 206 and can both share the same internal protective fluid. In some implementations, the same protective fluid can be shared among the motor 206, the protector 204, and the monitoring sub 108. The monitoring sub 108 has a housing 107 that protects electronics, cables, sensors, and other components inside the monitoring sub 108. A sensor 212 (for example, a microfluidic device) can be attached to an inner surface of the monitoring sub 108 under the housing 107, adjacent to or separate from the other electronics of the monitoring sub. The housing 107 can form a seal that protects the internal electronics of the monitoring sub from the high pressures at the wellbore. The monitoring sub 108 can transmit to the surface of the wellbore, through line 114, the status of the ESP assembly and other data. In some implementations, the monitoring sub can communicate wirelessly to the surface of the wellbore. Each of the components of the ESP assembly can have common or separate protective fluids that flow internally to protect moving parts and electronics of the components. The conditions at the wellbore cause the protective fluids to degrade. For example, water or other fluids can ingress the ESP assembly 200 and contaminate the fluid; wear of rotating components such as bearings or shafts can create particle contamination; or fluid temperature in excess of allowable range or outgassing of downhole electronic components may degrade the protective fluid Referring to FIG. 3, a partial, cross-sectional view of a portion of the ESP assembly is shown. In this embodiment, an internal shaft 300 of the ESP assembly extends through the ESP motor 204 and the monitoring sub 108. In the interest of simplicity, bearings, seals, valves, and other internal components of the ESP assembly are not shown. The ESP motor 204 includes a rotor 304 and a stator 302. The shaft 300, rotor 304, bearings, and other components can be lubricated by the protective fluid 306 that flows around the shaft 300 and the rotor 304. The protective fluid 306 can flow through lubricating holes 308 or grooves of the shaft or of a surface around the shaft to allow the fluid 306 to flow from one side of the shaft to another, and to the rotor 304. The protective fluid 306 can be a dielectric fluid (for example, a liquid dielectric insulator) or a hydraulic fluid (for example, a lubricating hydraulic oil). Multiple protective fluids can flow inside the ESP assembly. The protective fluid 306 also flows around the portion of the shaft 300 if disposed within the monitoring sub 108. The protective fluid 306 can be exposed to a sensor 312 attached to an inner surface of the monitoring sub 108 or to any component of the ESP assembly. As further discussed below, the protective fluid 306 can be moved by a fluid moving device 310 or by any other technique to reach the sensor 312.

Figure 3:
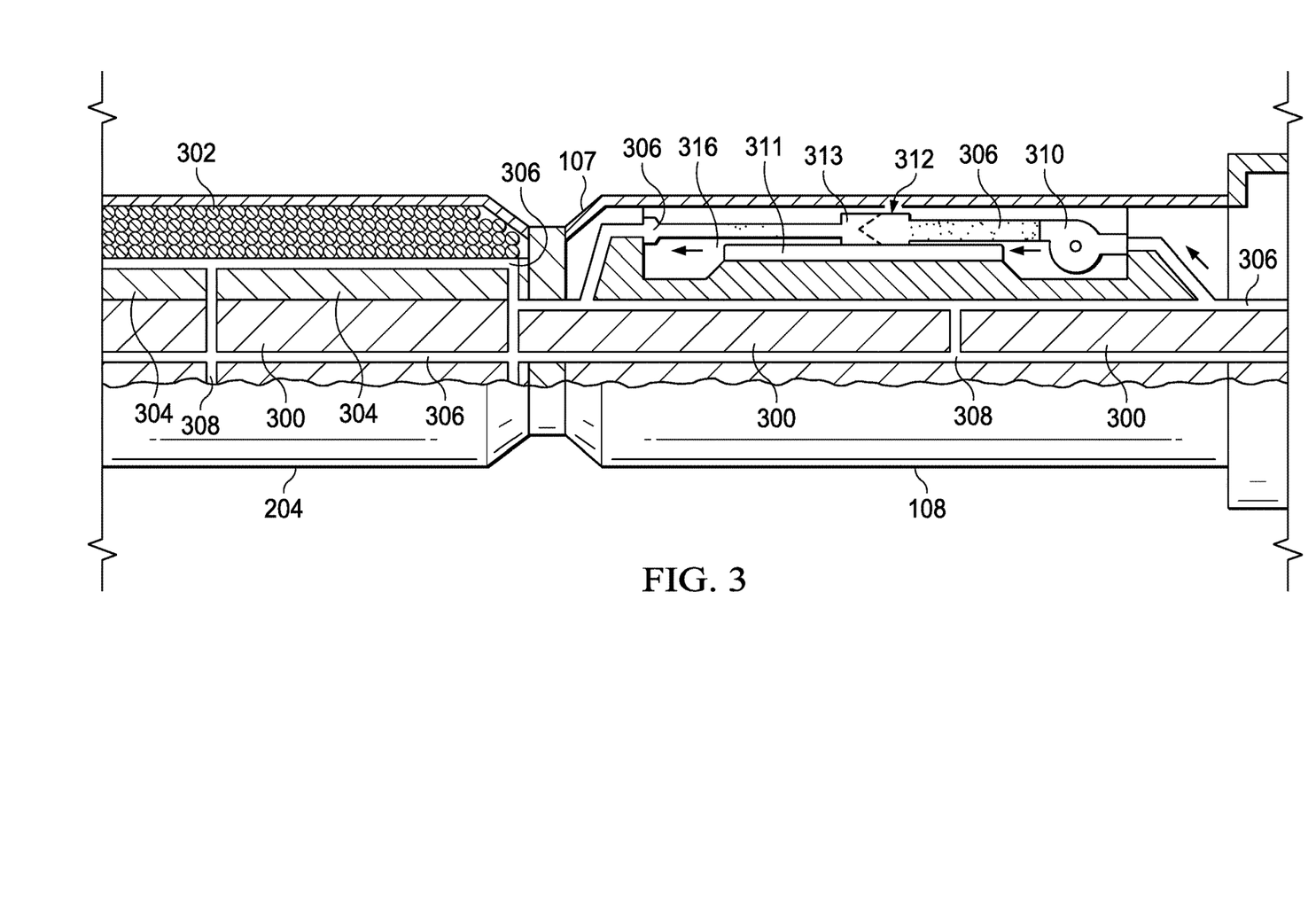
FIG. 3 shows a partial cross-sectional view of an ESP and a monitoring sub according to implementations of the present disclosure.

The sensor 312 includes a microfluidic analyzer that includes a microfluidic device. In some implementations, the microfluidic analyzer can include micro-electro-mechanical systems (MEMS) to perform operations such as pumping fluid, mixing two fluids, heating fluids or other operations. Alternatively or in addition, the microfluidic analyzer can include passive devices, for example, valves, vias, or similar features, that can be coupled to actuators, for example, pumps, mixers or similar actuators, to perform operations including analyzing the degradation level of the fluids. For example, the microfluidic analyzer or components of the microfluidic analyzer can be obtained from RAB-Microfluidics Ltd., located in Aberdeen, UK. The microfluidic analyzer includes one or more channels to receive the fluid. The channel is formed on a substrate made of glass, silicon wafer or polydimethoxysilane (PDMS), for example. MEMS-based actuators are built into the substrate near each channel or actuators are separately connected to the substrate and fluidically coupled to the channel (or both). The sensor 312 can be configured to operate in a horizontal position. For example, in an ESP that operates in a horizontal wellbore, sensor 312 can be horizontally installed in the downhole tool (for example, along the longitudinal axis of the ESP), as shown in FIG. 3. For installation in a vertical well, the sensor 312 can be installed perpendicular to the longitudinal axis of the ESP. Additionally, the sensor 312 can be mechanical isolated by an insulator (for example, a gel or a foam) from the downhole tool to improve the reliability of the measurements.

To monitor a level of degradation of the protective fluid 306, a portion of the sensor 312 is exposed to the protective fluid 306. One or more of these sensors 312 can be rigidly attached to any tool cavity 316 accessible by the protective fluid 306. For example, the sensor 312 can be attached to an inner surface of the ESP 104 along a fluid path of the protective fluid 306. As shown in FIG. 3, the sensor 312 is mounted to and communicatively coupled with the monitoring sub 108 to transmit information to the monitoring sub 108. For example, the sensor 312 can have an electronic board 311 communicatively connected to the monitoring sub 108. The sensor 312 has a body 313 that is exposed and responsive to the protective fluid 306 (for example, a portion of the protective fluid) flowed through the body of the sensor to analyze the protective fluid and determine the level of degradation. The portion of the protective fluid 306 is exposed to the body 313 of the sensor 312 responsive to the sensor 312 or a fluid moving device 310 moving the fluid through the body 313 of the sensor 312. The sensor 312 can be disposed along the natural path of the protective fluid 306 or external to the path of the protective fluid 306, in which cases the fluid moving device 310 can direct the protective fluid 306 toward the sensor. In some implementations, the sensor 312 can be submerged, by a mechanism of the monitoring sub, in the protective fluid 306 to expose the sensor to the fluid. The body 313 of the sensor 312 can sense the protective fluid 306 as the fluid moves across a surface of the body. The sensor 312 can analyze and determine, at least in part, the degradation level of the protective fluid 306 and transmit the degradation level to the monitoring sub 108. For example, responsive to sensing the fluid, the sensor 312 can transmit at least one of a voltage output, a pressure output, and a temperature output to the monitoring sub 108. The monitoring sub 108 can transmit the degradation level to a surface of the wellbore to be further analyzed or processed, if necessary.

To expose the sensor 312 to the protective fluid 306, a fluid moving device 310 can flow a portion of the fluid across a body 313 of the sensor 312. The body 313 of the sensor is configured to be responsive to the fluid. In some implementations, the fluid moving device 310 can be a small displacement pump such as a peristaltic pump. In some implementations, the fluid moving device 310 can be a micro-pump that moves the fluid with a natural, positive intake pressure, or a vacuum pump that moves the fluid with a negative pressure force on the discharge end of the sensor 312. In some examples, the fluid moving device 310 can be an Archimedes screw-type pump. The protective fluid 306 can be actively or passively circulated through the surface of the sensor 312. The fluid moving device 310 can be powered by a power source of the ESP assembly (not shown) or can have its own power source (for example, battery). In some implementations, the protective fluid 306 can be moved through a sensory convection current or oil convection current. For example, the protective fluid 306 can move due to thermal heating and cooling of the protective fluid 306 that sets up a fluid convection current. The fluid convection current can enable a circulation of the fluid 306 over the sensor.

The sensor 312 can determine the level of degradation of the protective fluid 306 using various methods, and transmit the results with different outputs. For example, the output of the determination performed by the sensor 312 can be a voltage, a pressure, or a temperature. For example, an optical source (such as a laser or light emitting diode) of determined wavelength can be mounted to the monitoring sub 108. The optical source can irradiate the fluid sample in the sensor with light of the determined wavelength so that the dielectric fluid exhibits fluorescence. An intensity of the fluorescence will vary based on contaminants in the fluid. A photometer mounted to the monitoring sub 108 and coupled to the optical source and the sensor will capture that intensity and convert it into a voltage signal. Thus, the output of the sensor can be a magnitude of the voltage signal, which is directly proportional to the intensity of the fluorescence. In some implementations, the sensor 312 (for example, the microfluidic device) can perform a portion of the determination and sent that information to the surface, where a receiver (see FIG. 1) can perform another portion of the determination. In some implementations, much of the analysis can be trend analysis over time rather than qualitative analysis. For example, fluid degradation can be measured as a change in an output voltage and compared to a laboratory generated degradation curve of the same fluid.

The sensor 312 can determine the degradation level using at least one of an inductance detection technique and a capacitance change technique. For example, sensor 312 includes a microfluidic analyzer with conductors, magnets, or other components that allow the microfluidic analyzer to sense a change of inductance or capacitance as a portion of the fluid 306 is flowed through the microfluidic analyzer.

Figure 4A:
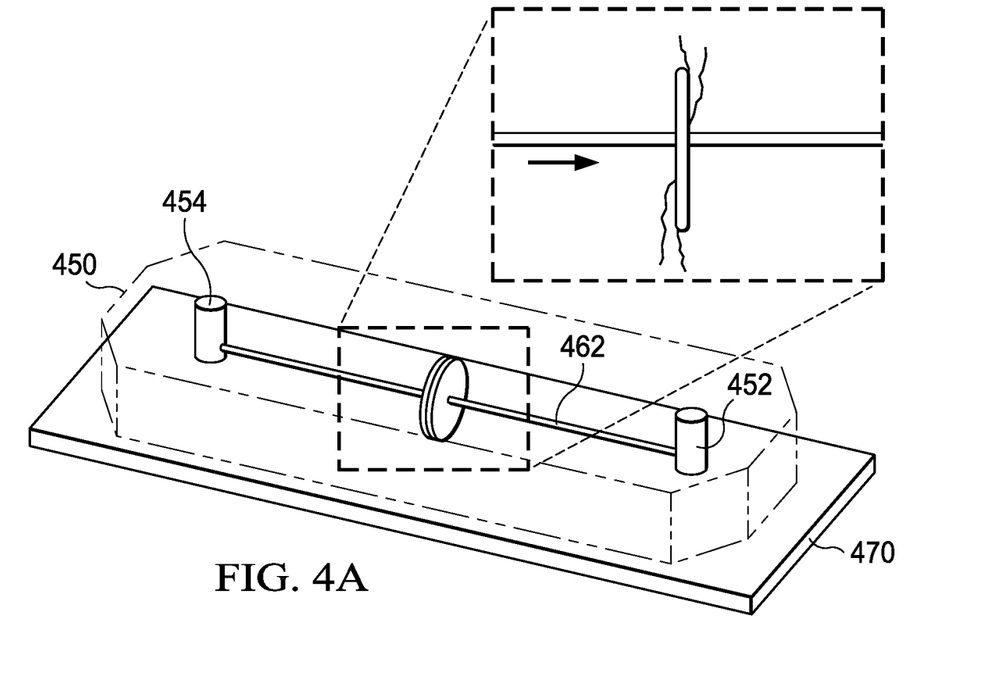
FIGS. 4A-4C show a microfluidic device used in an inductance detection method.
Figure 4B:
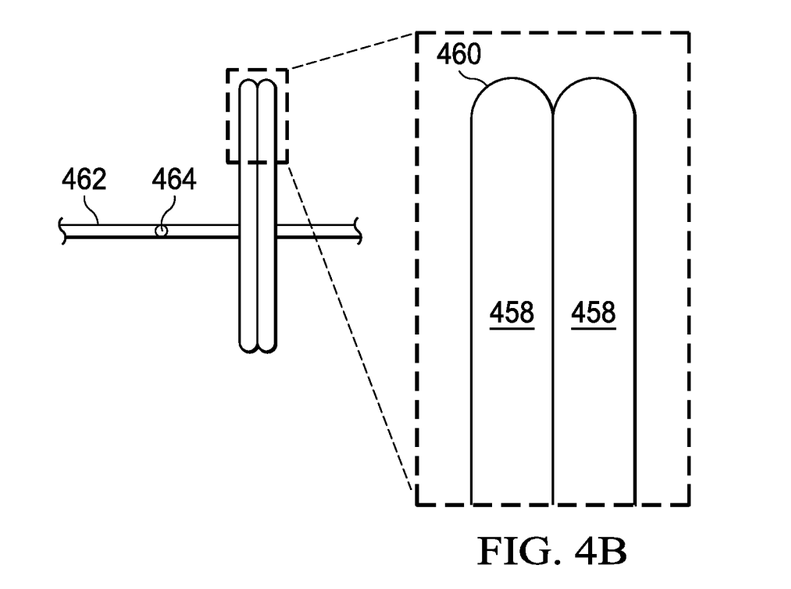
Figure 4C:
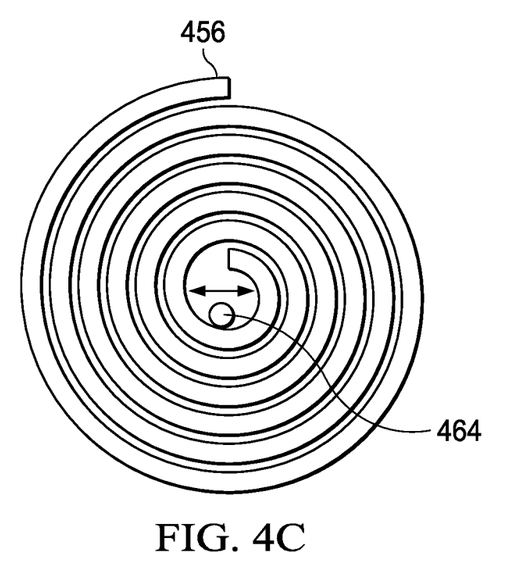

Referring to FIGS. 4A-4C, another technique for detecting particle contamination includes an inductance detection technique. For example, a microfluidic chip 470 can be used to determine the particle contamination level. The microfluidic chip 470 can include an impedance sensor 450 having an internal micro-channel 462 surrounded by two single-layer coils 458 and 460. Particles 464 of the protective fluid can be moved by the pump (see FIG. 3) from an inlet 454 of the microfluidic chip to an outlet 452 of the microfluidic chip. The particles 464 can be passed through the micro-channel 462 to be sensed by the coils 458 and 460 to provide a change in inductance and a measurable increase in the signal to noise ratio. The results can be analyzed by the microfluidic device or external circuitry to provide a particle count to the surface of the wellbore. Sampling can be done continuously or intermittently. The micro-channel can have a diameter of about 300 μm, and the coil wire can have an outer diameter of about 900 μm.

Figure 5:
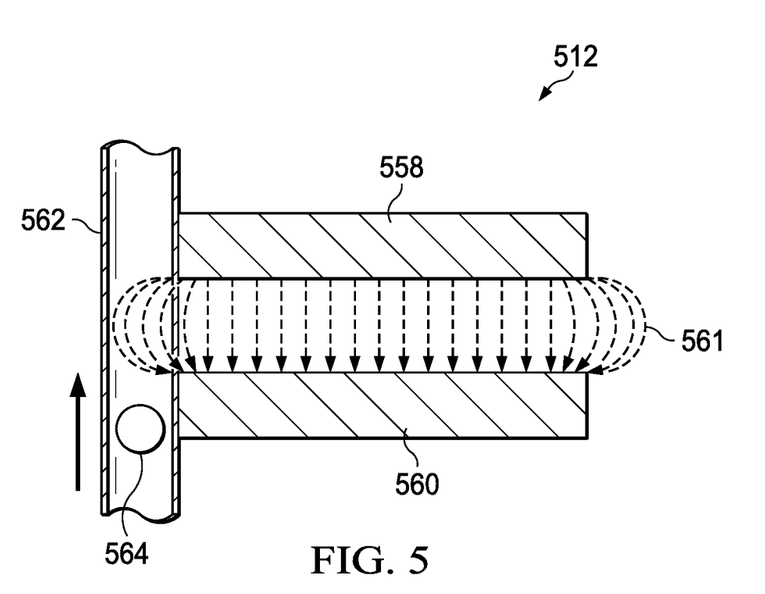
FIG. 5 is a side view of a portion of a microfluidic device used in a capacitance change method.

FIG. 5 shows a similar method to the one described in FIGS. 4A-4C for detecting fluid contamination. Water particles contaminating the protective fluid can be detected using capacitance change. A microfluidic circuit 512 has a micro-channel 562 for particles 564 to move along the channel similar to the inductive circuit and sensor described above with respect to FIGS. 4A-4C. The microfluidic circuit 512 has two capacitance plates 558 and 560 parallel to one another to form an electric field 561 between the plates. As a water particle 564 moves adjacent to the plates, a capacitance between the plates changes. The change in capacitance can be analyzed by the microfluidic device or external circuitry to provide the change to the surface of the wellbore. Sampling can be done continuously or intermittently.

Figure 6:
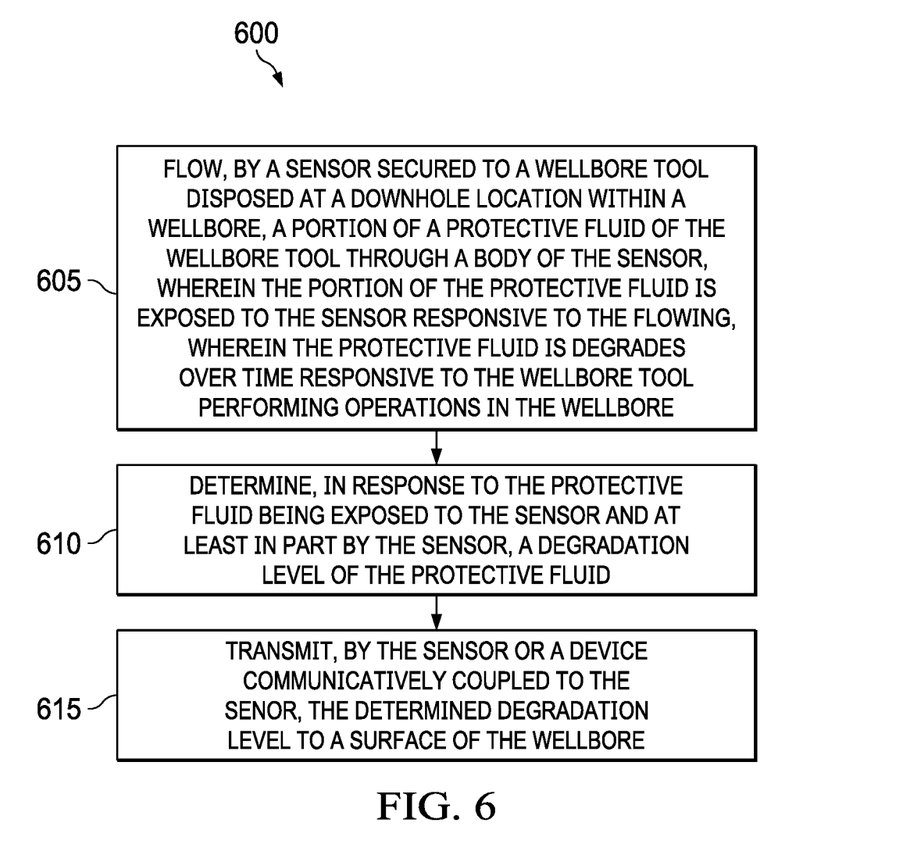
FIG. 6 is a flowchart showing a method of monitoring a protective fluid of a wellbore tool.

FIG. 6 shows a flowchart of a method 600 of monitoring a protective fluid of a wellbore tool. The method includes flowing, by a sensor secured to a wellbore tool disposed at a downhole location within a wellbore, a portion of a protective fluid of the wellbore tool through a body of the sensor, where the portion of the protective fluid is exposed to the sensor responsive to the flowing, where the protective fluid degrades over time responsive to the wellbore tool performing operations in the wellbore (605). The method also includes, in response to the protective fluid being exposed to the sensor, determining, at least in part by the sensor, a degradation level of the protective fluid (610). The method also includes transmitting, by the sensor or a device communicatively coupled to the sensor, the determined degradation level to a surface of the wellbore (615).

Although the following detailed description contains many specific details for purposes of illustration, it is understood that one of ordinary skill in the art will appreciate that many examples, variations, and alterations to the following details are within the scope and spirit of the disclosure. Accordingly, the example implementations described herein and provided in the appended figures are set forth without any loss of generality, and without imposing limitations on the claimed implementations. For example, the implementations are described with reference to an electric submersible pump (ESP). However, the disclosure can be implemented with any wellbore equipment that has a protective fluid susceptible to degradation.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, or to about another particular value or a combination of them. When such a range is expressed, it is to be understood that another implementation is from the one particular value or to the other particular value, along with all combinations within said range or a combination of them.

Throughout this application, where patents or publications are referenced, the disclosures of these references in their entireties are intended to be incorporated by reference into this application, in order to more fully describe the state of the art to which the disclosure pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present disclosure.

That which is claimed is:

1. A method of monitoring a protective fluid of a wellbore tool, the method comprising:
   flowing, by a sensor or a fluid moving device secured to a wellbore tool disposed at a downhole location within a wellbore, a portion of a protective fluid of the wellbore tool through a body of the sensor, wherein the portion of the protective fluid is exposed to the body of the sensor responsive to the flowing, wherein the protective fluid degrades over time responsive to the wellbore tool performing operations in the wellbore;
   in response to the protective fluid being exposed to the body of the sensor, determining, at least in part by the sensor, a degradation level of the protective fluid; and
   transmitting, by the sensor or a device communicatively coupled to the sensor, the determined degradation level to a surface of the wellbore.

2. The method of claim 1, wherein the sensor comprises a microfluidic device, and wherein determining the degradation level comprises analyzing, by the microfluidic device, the protective fluid to determine the degradation level of the protective fluid.

3. The method of claim 1, wherein flowing the portion of the protective fluid comprises setting up a convection current by heating and cooling the protective fluid.

4. The method of claim 1, wherein flowing the protective fluid comprises moving the fluid by at least one of a peristaltic pump or an Archimedes screw-type pump.

5. The method of claim 1, wherein the wellbore tool comprises an electric submersible pump (ESP) coupled to a monitoring sub on which the sensor is secured, the monitoring sub communicatively connected to the surface of the wellbore, and wherein transmitting the degradation level to the surface comprises sending, from the sensor, the degradation level to the monitoring sub, and sending, from the monitoring sub, the degradation level to the surface.

6. The method of claim 1, wherein the protective fluid comprises at least one of a dielectric fluid or a hydraulic fluid.

7. The method of claim 1, wherein transmitting the determined degradation level comprises transmitting at least one of a voltage output, a current output, a pressure output, a time stamp, or a temperature output of the sensor.

8. The method of claim 1, further comprising determining, at least in part by a surface processor at the surface of the wellbore, the degradation level of the protective fluid.

9. The method of claim 1, wherein the sensor comprises a microfluidic device, and wherein determining the degradation level comprises determining the degradation level using at least one of an inductance detection technique or a capacitance change technique.

10. The method of claim 9, wherein the microfluidic device is disposed along a flow path of the protective fluid, and wherein determining the degradation level of the protective fluid comprises using a fluid moving device to flow a portion of the protective fluid through a micro-channel of the microfluidic device.

11. The method of claim 9, wherein determining the degradation level comprises detecting a change in inductance and an increase in a signal to noise ratio of the microfluidic device as a portion of the protective fluid moves through a micro-channel of the microfluidic device using the inductance detection technique.

12. A system for monitoring a protective fluid, the system comprising:
a monitoring sub coupled to an electric submersible pump (ESP), the monitoring sub communicatively coupled to a surface of a wellbore; and
a microfluidic device communicatively connected to the monitoring sub, the microfluidic device configured to be exposed to a protective fluid of the ESP as a portion of the protective fluid is flowed through a body of the microfluidic device responsive to the protective fluid;
wherein the microfluidic device is configured to, at least in part, determine a degradation level of the protective fluid and transmit the degradation level to the monitoring sub to be transmitted, by the monitoring sub, to the surface of the wellbore.

13. The system of claim 12, further comprising a fluid moving device configured to move the protective fluid across a surface of the body of the microfluidic device.

14. The system of claim 13, wherein the fluid moving device comprises at least one of a peristaltic pump or an Archimedes screw-type pump.

15. The system of claim 12, wherein the protective fluid comprises at least one of a dielectric fluid or a hydraulic fluid.

16. The system of claim 12, wherein the protective fluid degrades over time responsive to the ESP performing operations in the wellbore.

17. The system of claim 12, wherein the microfluidic device is configured to transmit the determined degradation level by transmitting at least one of a voltage output, a current output, a pressure output, a time stamp, or a temperature output of the microfluidic device.

18. The system of claim 12, wherein the microfluidic device is configured to determine the degradation level using at least one of an inductance detection technique or a capacitance change technique.

19. The system of claim 18, wherein the microfluidic device is disposed along a flow path of the protective fluid, and wherein a fluid moving device is configured to flow a portion of the protective fluid through a micro-channel of the microfluidic device.

20. The system of claim 19, wherein the microfluidic device is configured to use the inductance detection technique, and wherein the microfluidic device is configured to determine the degradation level by detecting a change in inductance and an increase in a signal to noise ratio in the microfluidic device as a portion of the protective fluid moves through the micro-channel.

* * * * *